United States Patent
Namati et al.

(10) Patent No.: US 10,184,782 B2
(45) Date of Patent: Jan. 22, 2019

(54) FREQUENCY-DOMAIN OPTICAL COHERENCE TOMOGRAPHY WITH EXTENDED FIELD-OF-VIEW AND REDUCTION OF ALIASING ARTIFACTS

(71) Applicant: NINEPOINT MEDICAL, INC., Bedford, MA (US)

(72) Inventors: Eman Namati, Belmont, MA (US); Muhammad Al-Qaisi, Winchester, MA (US); Matthew A. Sinclair, Somerville, MA (US); Benedikt Graf, Cambridge, MA (US); David Vader, Brookline, MA (US)

(73) Assignee: NINEPOINT MEDICAL, INC., Bedford, MA (US)

( * ) Notice: Subject to any disclaimer, the term of this patent is extended or adjusted under 35 U.S.C. 154(b) by 38 days.

(21) Appl. No.: 14/278,424

(22) Filed: May 15, 2014

(65) Prior Publication Data
US 2014/0340689 A1   Nov. 20, 2014

Related U.S. Application Data

(60) Provisional application No. 61/824,687, filed on May 17, 2013.

(51) Int. Cl.
*G01B 9/02* (2006.01)
*A61B 5/00* (2006.01)

(52) U.S. Cl.
CPC ........ *G01B 9/02091* (2013.01); *A61B 5/0066* (2013.01); *A61B 5/0084* (2013.01)

(58) Field of Classification Search
CPC ............ G01B 9/02002; G01B 9/02004; G01B 9/02091; A61B 5/0066; A61B 5/0084
See application file for complete search history.

(56) References Cited

U.S. PATENT DOCUMENTS

| 7,733,497 B2 | 6/2010 | Yun | |
|---|---|---|---|
| 2003/0025913 A1* | 2/2003 | Izatt | A61B 5/0066 356/479 |

(Continued)

OTHER PUBLICATIONS

Choma M A et al: "Swept source optical coherence tomography using an all-fiber 1300-nm ring laser source", Journal of Biomedical Optics, S P I E—International Society for Optical Engineering, US, vol. 10, No. 4, Jul. 1, 2005, pp. 44009-1, XP002411522, ISSN: 1083-3668, Durham, North Carolina.

(Continued)

*Primary Examiner* — Michael A Lyons

(57) ABSTRACT

The present disclosure provides an OCT imaging system to reduce or eliminate frequency-domain aliasing artifacts. The frequency is shifted using a carrier frequency to define a sampling range substantially centered on the carrier frequency. An image of the sample is generated from a displayed imaging range that consists of a subset of the frequencies within the sampling range. Furthermore, the system may be configured to determine the carrier frequency such that a Nyquist frequency corresponding to the shifted frequency is extended beyond either an upper or a lower bound of an OCT quality envelope corresponding to the first portion of light. Additionally, the carrier frequency may be determined such that a lower bound of the OCT quality envelope is greater or less than a zero-frequency DC limit.

19 Claims, 12 Drawing Sheets

(56) References Cited

U.S. PATENT DOCUMENTS

2005/0171438 A1 8/2005 Chen
2014/0079248 A1* 3/2014 Short .................. G10L 21/0272
381/119

OTHER PUBLICATIONS

Choma, Michael et al., "Sensitivity advantage of swept source and Fourier domain optical coherence tomography", Optics Express, vol. 11, No. 18, Sep. 8, 2003, 2183-2189.

* cited by examiner

700

```
┌─────────────────────────────────────┐
│ Illuminate a sample with a first    │   710
│ portion of light.                   │
└─────────────────────────────────────┘
                  │
                  ▼
┌─────────────────────────────────────┐
│ Illuminate a reference plane with a │   720
│ second portion of light.            │
└─────────────────────────────────────┘
                  │
                  ▼
┌─────────────────────────────────────┐
│ Shift a frequency of the first      │
│ portion of light or the second      │   730
│ portion of light to define a        │
│ sampling range.                     │
└─────────────────────────────────────┘
                  │
                  ▼
┌─────────────────────────────────────┐
│ Generate a displayed imaging range  │   740
│ from the sampling range.            │
└─────────────────────────────────────┘
```

*Figure 7*

FREQUENCY-DOMAIN OPTICAL COHERENCE TOMOGRAPHY WITH EXTENDED FIELD-OF-VIEW AND REDUCTION OF ALIASING ARTIFACTS

CROSS REFERENCE TO RELATED APPLICATIONS

This application claims the benefit of U.S. Provisional Application Ser. No. 61/824,687 filed May 17, 2013, entitled "Frequency-Domain Optical Coherence Tomography with Extended Field-of-View and Reduction of Aliasing Artifacts," which application is incorporated herein by reference in its entirety.

TECHNICAL FIELD

In various embodiments, the present disclosure relates to optical imaging systems, in particular optical imaging systems utilizing frequency-domain interferometry.

BACKGROUND

Frequency-domain (or "swept-source") optical coherence tomography (OCT) systems are powerful tools that provide non-invasive, high-resolution images of biological samples at higher acquisition speeds and lower signal-to-noise ratios than time-domain OCT systems. FIG. 1 illustrates an exemplary frequency-domain OCT system 100 at a high level. As shown, the exemplary OCT system includes a wavelength-swept laser source 95 (also referred to herein as a frequency swept source) that provides a laser output spectrum composed of single or multiple longitudinal modes to an input of a coupler 72. The coupler 72 divides the signal fed thereto into the reference arm 80 that terminates in the reference mirror 82 and the sample arm 84 that terminates in the sample 86. The optical signals reflect from the reference mirror 82 and the sample 86 to provide, via the coupler 72, a spectrum of signals that are detected by a photodetector 88.

FIG. 2 is a plot 200 graphically illustrating a detection and ranging-depth arrangement for a typical frequency-domain OCT system, such as, for example, the system 100 of FIG. 1. As depicted, an envelope of coherence function 210 (or "fringe visibility curve") defined by the instantaneous output spectrum of the swept source and the detection frequency of the system is plotted in the frequency domain. In this example, both the source output spectrum and the fringe visibility curve are Gaussian. As will be appreciated, the positive and negative frequency bands are not differentiable in the electrical domain. Accordingly, the images associated with the positive and negative frequency bands, respectively, are overlapped. As a result of this ambiguity, only half of the frequency range, corresponding to positive depth, is used for the imaging range 220. The upper frequency bound of the imaging range 220 is typically matched to the 6 dB roll-off (Zc) of the coherence function 210, which is referred to as the ranging depth.

The limitation on ranging depth (or the imaging depth range) illustrated in FIG. 2 has been ameliorated to some extent via the incorporation of the carrier-frequency heterodyne detection scheme described in U.S. Pat. No. 7,733,497 (the '497 patent), the entire disclosure of which is incorporated by reference herein. FIG. 3 is a plot 300 graphically illustrating a shifting of the frequency band by a carrier frequency (fs) 301 in accordance with the scheme of the '497 patent. As depicted, an envelope of coherence function 310 is shown. The function 310 is defined by the instantaneous output spectrum of the swept source and the detection frequency band, wherein the frequency band is shifted by the carrier frequency 301. As will be appreciated, this shifting doubles the ranging depth 320, as both sides of the frequency band centered at the carrier frequency (fs) 301 produce images without ambiguity. Additionally, as shown, the Nyquist frequency ($f_{nyquist}$) 303 is typically double the carrier frequency (fs) 301. Furthermore, the Nyquist frequency, as known in the art, may be one-half of the sampling rate of the system.

However, artifacts that result in sub-optimal imaging may in some circumstances, plague even such carrier-frequency heterodyne detection schemes. For example, FIG. 4, shows the plot 300 and further illustrates foldover artifacts 331 (i.e., aliasing artifacts). The artifacts 331 may result from portions of the coherence function 310 beyond the DC (i.e., frequency=0) limit and/or the Nyquist frequency limit. Furthermore, the artifacts 331 may manifest even when the frequency band has been shifted by a particular carrier frequency (fs) 301. Such artifacts may be caused by reflections from structures outside of the imaging range of the system (due to, e.g., non-optimal sample placement) and may lead to aberrations in the OCT images. Thus, there is a need for frequency-domain OCT systems and techniques that eliminate such aliasing artifacts while enabling larger imaging ranges.

BRIEF DESCRIPTION OF THE DRAWINGS

FIG. 7 is a logic flow for optically imaging a sample utilizing a frequency-domain OCT system in accordance with the present disclosure.

DESCRIPTION OF EMBODIMENTS

Figure 1:
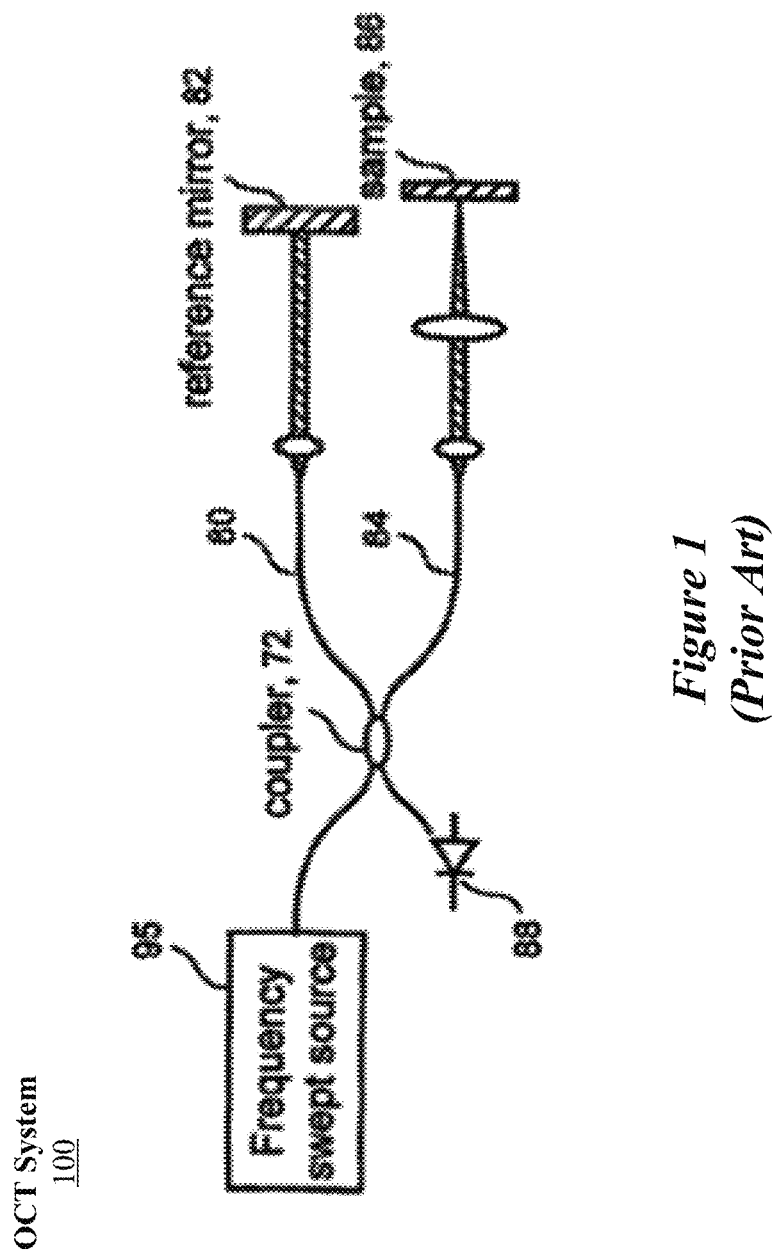
FIG. 1 illustrates a block diagram of a frequency-domain OCT system.
Figure 2:
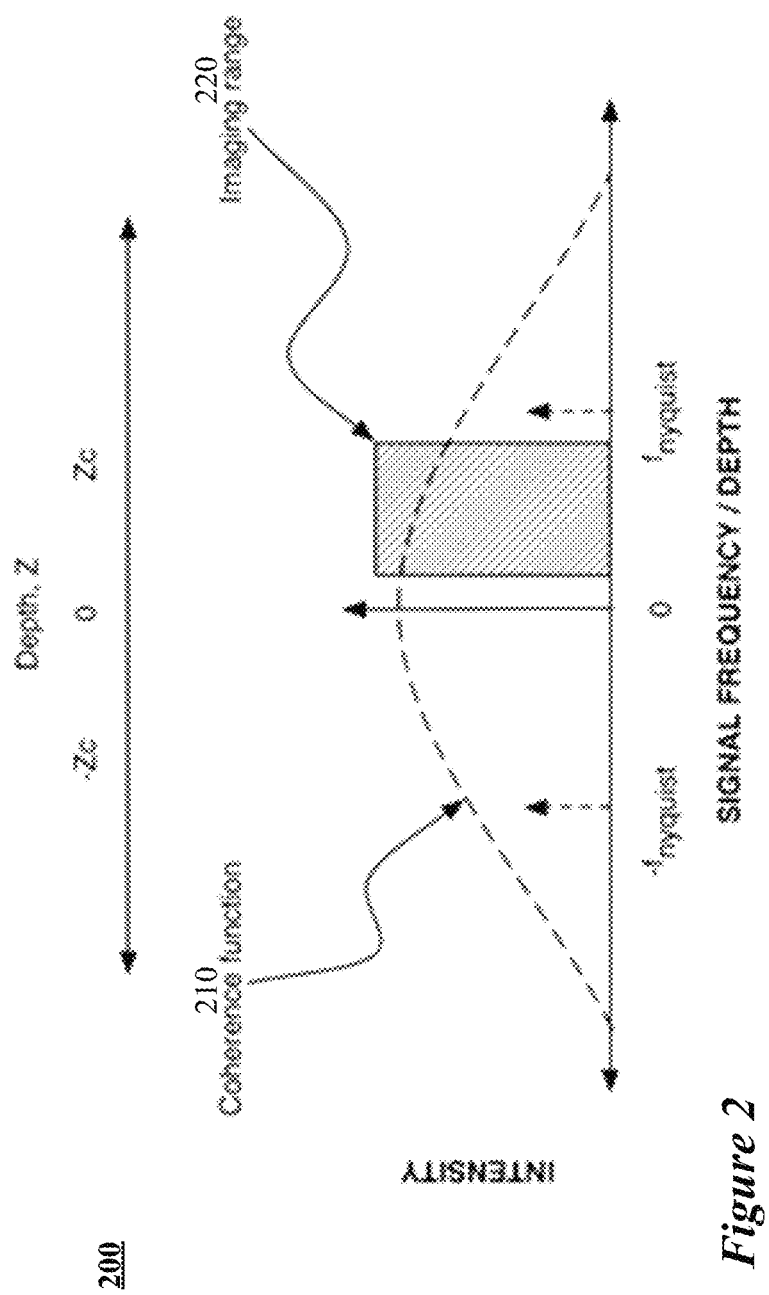
FIG. 2 illustrates a plot of a coherence function and associated imaging range.

In general, embodiments of the present disclosure may be implemented to reduce or eliminate aliasing artifacts in frequency-domain OCT systems. In particular, the present disclosure may be implemented to improve OCT image quality.

With some examples, an image of a sample may be acquired using a frequency-domain OCT system wherein the frequency is shifted using a carrier frequency to define a sampling range substantially centered on the carrier frequency. The system may generate an image of the sample over a displayed imaging range that consists of a subset of the frequencies within the sampling range. Said differently, a displayed imaging range may be generated wherein the displayed imaging range corresponds to a subset of the range of frequencies within the sampling range. Furthermore, the system may be configured to determine the carrier frequency such that a Nyquist frequency corresponding to the shifted frequency is extended beyond either an upper or a lower bound of an OCT quality envelope. Additionally, the carrier frequency may be determined such that a lower bound of the OCT quality envelope is greater or less than a zero-frequency DC limit.

Accordingly, an image of a sample can be acquired using a frequency-domain OCT system wherein foldover artifacts are not aliased at least until they reach the outer bounds of the sampling imaging range. The displayed imaging range is then generated from a subset of the frequencies in the sampling range to reduce and/or substantially eliminate foldover artifacts.

It is important to note, however, that the disclosed systems and methods may be embodied in many different forms and should not be construed as limited to the embodiments set forth herein. Rather, these embodiments are provided so that this disclosure will be thorough and complete, and will fully convey the scope of the claims. In the drawings, like numbers refer to like elements throughout.

Figure 5:
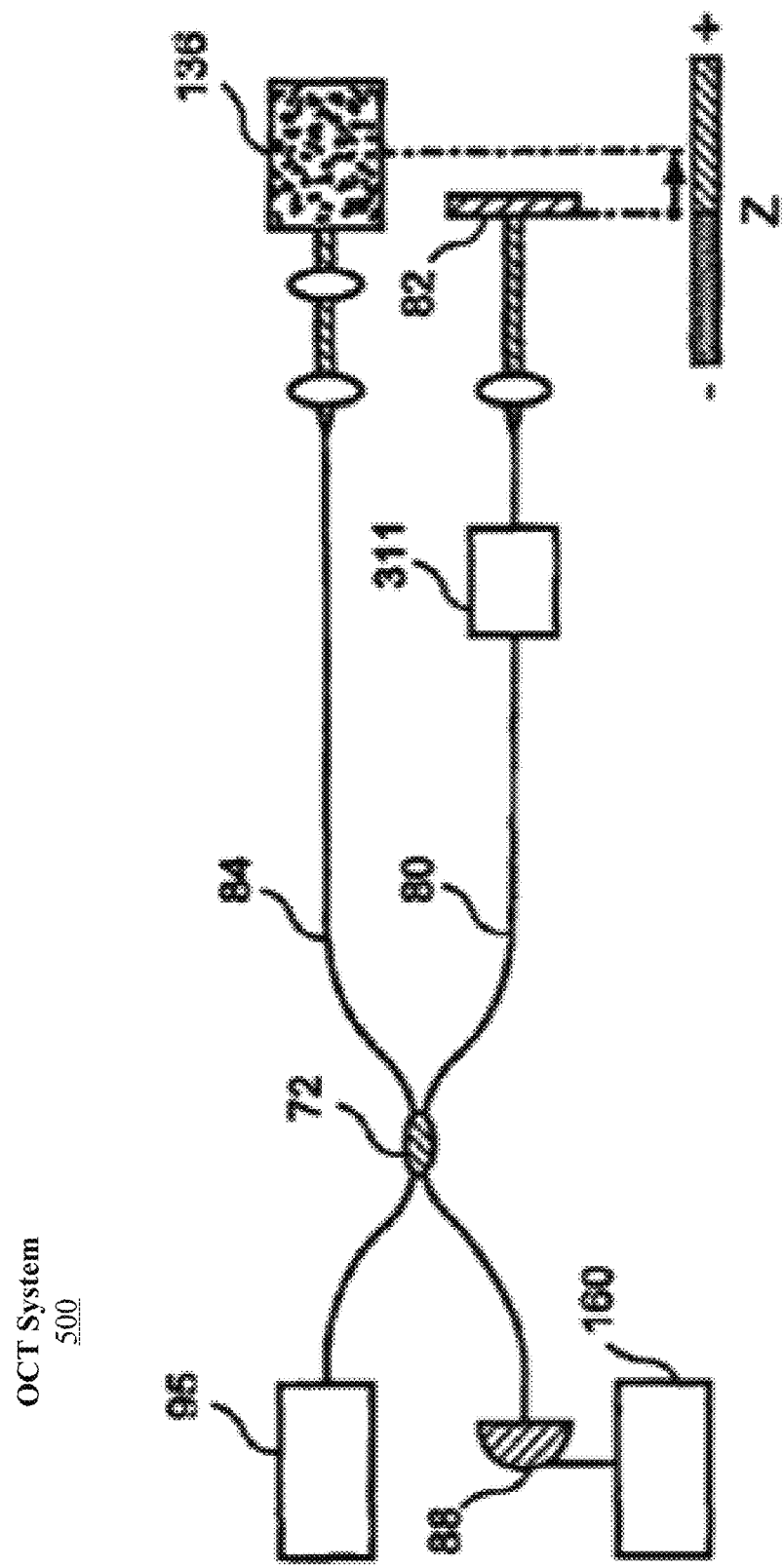
FIG. 5 illustrates a block diagram of a frequency-domain OCT system arranged according to at least one embodiment of the present disclosure.

FIG. 5 shows a high level diagram of a frequency-domain OCT system 500, arranged according to embodiments of the present disclosure. The system 500 may be implemented to generate an image of a sample as described above. In particular, the system 500 may be implemented to select a carrier frequency for shifting the signal frequency band such that an OCT quality envelope corresponding to the shifted frequency band is within the bounds of the zero-frequency DC limit and the Nyquist frequency limit. This will be explained in greater detail below.

The system 500 includes a wavelength-swept light source 95 that provides a light having an output spectrum composed of single or multiple longitudinal modes. The source 95 provides the light to an input of a coupler 72. The coupler 72 divides the signal fed thereto into a reference arm 80 and a sample arm 84. The reference arm 80 terminates in the reference mirror 82, also referred to as a reference plane. The sample arm terminates in a sample 136. Optical images reflected from the sample 136 and the reference mirror 82 are received by a photodetector 88 and processed by a signal processor 160.

Additionally, the system 500 includes a single mode-fiber interferometer employing an optical frequency shifter 311 in the reference arm 80. In some examples, The frequency shifter 311 may include or consist essentially of, for example, an acousto-optic frequency shifter, as described in the '497 patent. The optical frequency shifter 311 in the reference arm 80 shifts the signal frequency band by a carrier frequency as described above. The signal processor 160 demodulates the carrier frequency. With some examples, the frequency shifter 311 is in the sample arm (not shown). In some examples, multiple frequency shifters 311 are provided (not shown) with a frequency shifter 311 disposed in both the reference arm 80 and the sample arm 84.

In general, the signal processor 160 is configured to receive light reflected from the reference plane 82 and the sample 136. More particularly, light emitted from the source 95 is reflected from the sample 136 and the reference plane 82 and received by the signal processor 160. The signal processor 160 is configured to receive this reflected light and generate the displayed image range from the sample range. In particular, the signal processor 160 is configured to omit frequencies from the set of frequencies corresponding to the sample range to form the displayed image range. In some examples, the signal processor 160 may include a band-pass filter. The band-pass filter may include both a high-pass filter and a low-pass filter. The high-pass filter may be implemented to reduce DC noise. Likewise, the low-pass filter may be utilized as an anti-aliasing filter. That is, the low-pass filter may be implemented to filter out frequencies higher than the bounds of the coherence function that might result in aliasing artifacts. As such, the low-pass filter may reduce aliasing artifacts.

The signal processor 160 may be realized as software, hardware, or some combination thereof. The processor may also include a main memory unit for storing programs and/or data relating to the methods described herein. The memory may include random access memory (RAM), read only memory (ROM), and/or FLASH memory residing on commonly available hardware such as one or more ASICs, FPGAs, electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, or other storage devices.

For embodiments in which the functions of the processor are provided by software, the program may be written in any one of a number of high-level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

Figure 6:
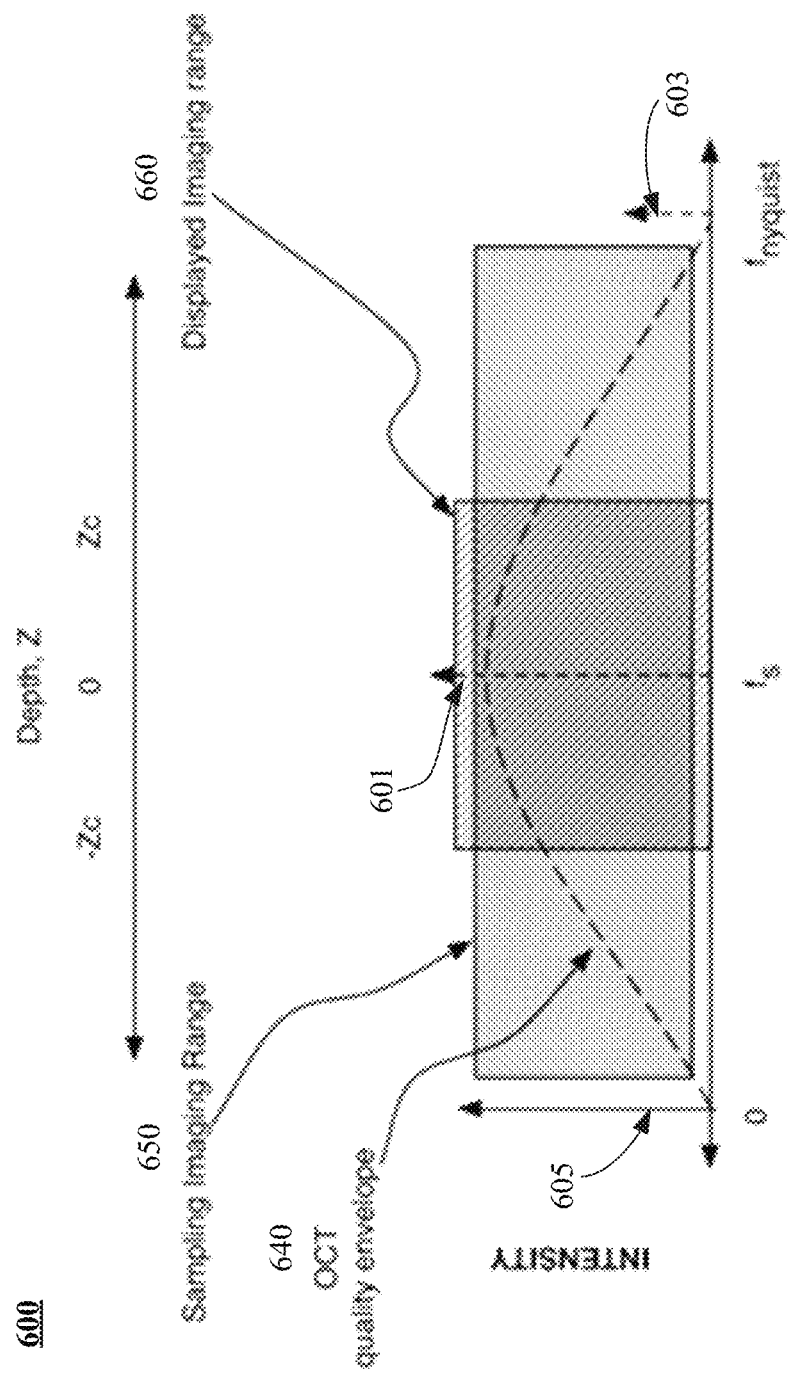
FIG. 6 illustrates a plot of a sampling range and corresponding displayed imaging range in accordance with the present disclosure.

FIG. 6 is a plot 600 graphically illustrating a shifting of the frequency band by a carrier frequency (fs) 601 in accordance with the present disclosure. In general, the carrier frequency (fs) 601 has been selected to extend the Nyquist frequency ($f_{nyquist}$) 603 beyond an upper bound of an OCT quality envelope 640. As used herein, the OCT quality envelope corresponds to an intensity envelope of frequencies. In some examples, the OCT quality envelope may be bounded by the 6 dB roll-off in measured intensity from the sample.

As will be appreciated, the OCT quality envelope 640 is related to and may be dependent upon a variety of properties. In particular, the OCT quality envelope 640 may be related to: the coherence function of the swept source; properties of the optical beam illuminating the sample 136, that is properties of the light emitted from the frequency-swept light source 95; the working distance, the waist, and/or the shape of the emitted light; and/or properties of the sample 136 being illuminated, such as, for example, scattering and/or absorption properties of the sample 136.

As depicted in FIG. 6, the OCT quality envelope 640 is substantially centered about the displayed imaging range. Accordingly, the imaging depth range can be decoupled into (a) a sampling imaging range 650 and (ii) a displayed imaging range 660. More specifically, the imaging range can be split into a sampling range 650, which corresponds to the depth range of all sampled points. In particular, the sampling range 650 may correspond to substantially all of the depths defined by the frequencies of the OCT quality envelope 640; while the displayed imaging range 660 corresponds to the depth range displayed by the OCT system. That is, the displayed imaging range 660 corresponds to a subset of the set of frequencies of the sampling range 650.

With some examples, the present disclosure provides selection of the carrier frequency (fs) 601 such that the sampling range 650 is defined between the DC limit 605 and the Nyquist limits 603. The imaging range 660 is generated from the sampling range to reduce and/or substantially eliminate foldover artifacts. More specifically, depths (and corresponding frequencies) outside of the displayed imaging range are not aliased at least until they reach the outer bounds of the sampling imaging range. Additionally, fixed pattern noise arising near the DC limit 605 and the Nyquist limits 603 are advantageously reduced or eliminated. As utilized herein, fixed pattern noise is defined as noise that does not exhibit a relationship with the frequencies representing the sample. That is, noise that has an approximately fixed frequency that is independent of the detected sample frequencies.

FIG. 7 is a block diagram of an example logic flow that may be performed by various portions of the system 500 of FIG. 5. In particular, the logic flow depicts aspects of a method for optically imaging a sample utilizing a frequency-domain OCT system. It is to be appreciated that although the present disclosure describes the logic flow with reference to the system 500 of FIG. 5, this is not intended to be limiting. For example, the logic flow may be implemented with an OCT system having a different configuration than the OCT system 500.

Referring now to FIG. 7, a flow diagram illustrating an exemplary method 700 in accordance with the present disclosure is shown. In particular, the method 700 depicts a logic flow for optically imaging a sample utilizing a frequency-domain optical coherence tomography (OCT) system comprising a wavelength-swept light source. The method 700 may begin at block 710.

At block 710, illuminate a sample with a first portion of light; a sample is illuminated with a first portion of light emitted by a wavelength-swept light source. For example, the wavelength-swept light source 95 may illuminate the sample 136 with a first portion of light emitted by the source 95.

Continuing from block 710 to block 720, illuminate a reference plane with a second portion of light; a reference plane is illuminated with a second portion of light emitted by the wavelength-swept light source. For example, the wavelength-swept light source 95 may illuminate the reference mirror 82 with a second portion of light emitted by the source 95.

It is to be appreciated, that the wavelength-swept light source 95 may emit multiple modes and/or frequencies of light. The emitted light may be divided into a first portion and a second portion by the coupler 72. The first portion and second portion of the emitted light is presented to the sample arm 84 and the reference arm 80, respectively, to illuminate the sample 136 and the reference mirror 82.

Continuing from block 720 to block 730, shift a frequency of the first portion of light or the second portion of light to define a sampling range; a frequency of at least one of the first portion of light or the second portion of light is shifted to define a sampling range including a set of frequencies. For example, the optical frequency shifter 311 may shift the signal frequency band by a carrier frequency to define a sampling range. More specifically, the optical frequency shifter 311 may shift the signal frequency band by the carrier frequency 601 to define the sampling range 650.

Continuing from block 730 to block 740, generate a displayed imaging range from the sampling range; a displayed imaging range consisting essentially of only a subset of the set of frequencies within the sampling range is generated. For example, the signal processor 160 may generate the displayed imaging range by omitting frequencies within the sampling range where aliasing and/or foldover occurs.

Referring again to FIG. 6, as depicted, the sampling range 650 extends from a first frequency to a second frequency and is substantially centered on the carrier frequency 601. Furthermore, the second frequency is larger than the first frequency.

Additionally, the displayed imaging range 660 extends from a third frequency larger than the first frequency to a fourth frequency smaller than the second frequency and is also substantially centered on the carrier frequency 601.

Figure 8:
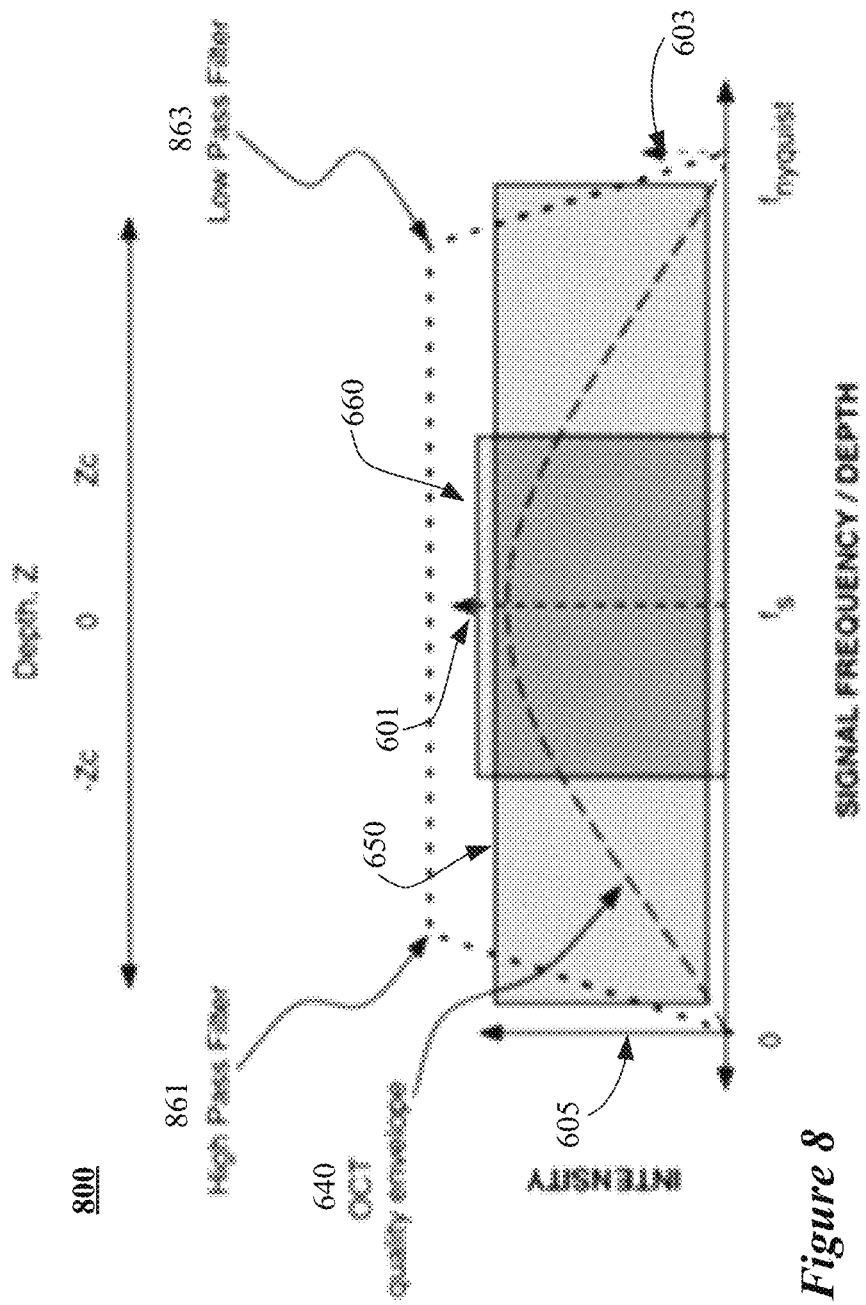
FIG. 8 illustrates another plot of a sampling range and corresponding displayed imaging range in accordance with the present disclosure.

As noted above, in some examples, the frequency-domain OCT system 500 may include band-pass filters. FIG. 8 is a plot 800 graphically illustrating an embodiment of the present disclosure incorporating a band-pass filter. In particular, the plot 800 illustrates incorporating both a high-pass filter 861 and a low-pass filter 863. As will be appreciated, in the plot 800, low frequencies represent shallow depths while high frequencies represent deeper depths.

Furthermore, it will be appreciated that in some OCT applications, or more particularly with some OCT systems, reflections may be caused by the imaging optics. These reflections may result in image degradation, such as, for example by producing peaks at lower frequencies or, more problematically, peaks folded in from the positive/negative depth ambiguity and overlaid onto the displayed imaging range 660.

Figure 9:
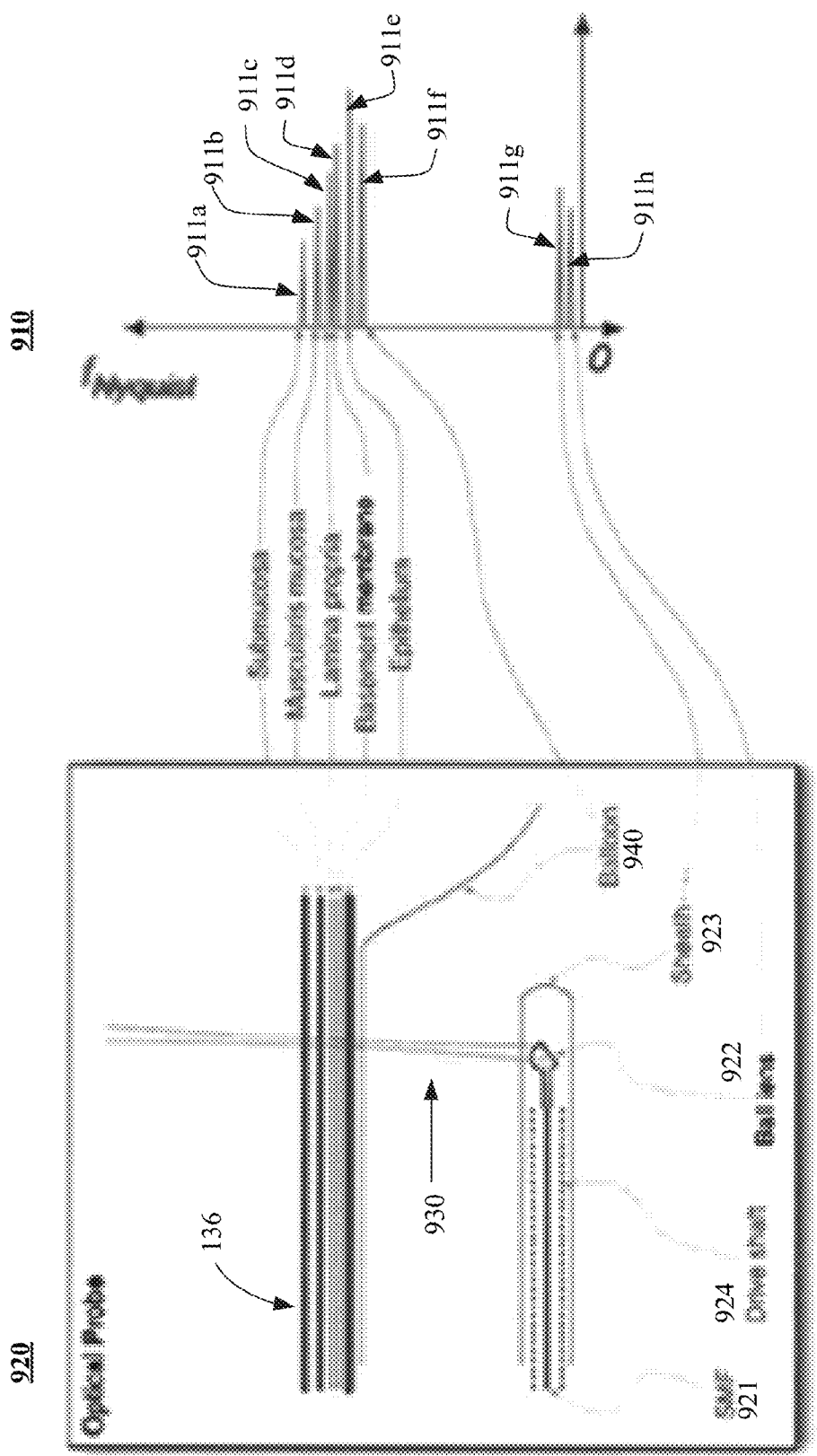
FIG. 9 illustrates an example OCT probe and corresponding frequency scan.

For example, FIG. 9 depicts a sample scan 910 performed by an exemplary probe 920. The probe 920 may be disposed on the sample arm of an OCT system (e.g., the sample arm 84). The probe 920 includes a fiber 921 (e.g., single mode fiber (SMF)) optically coupled to a lens 922. The fiber 921 and the lens 922 are disposed in a sheath 923. A drive shaft 924 is coupled to the lens 922 to cause the lens 922 to rotate and expose the sample 136 with light 930. The probe 920 may further include a balloon 940 used in the imaging process.

As can be seen from the sample scan 910, frequency peaks 911*a* to 911*h* are shown. These frequency peaks correspond to light reflected back from the sample 136 and also from the probe 920. In particular, the peaks 911*a* to 911*e* may correspond to reflections from the sample 136 while peaks 911*f* to 911*h* may correspond to reflections of the probe. In particular, the peak 911*f* may correspond to a reflection from the balloon 940; the peak 911*g* may correspond to a reflection from the sheath 923; and the peak 911*h* may correspond to a reflection from the lens 922.

Returning to FIG. 8, the high-pass filter may be configured to filter out one or more of the peaks 911. In particular, the high-pass filter 861 may be configured to filter out those peaks 911, such as, for example, the peaks 911*f* to 911*h*. In some examples, the peaks 911 may correspond to shallower depths as discussed on conjunction with FIG. 10.

Figure 10:
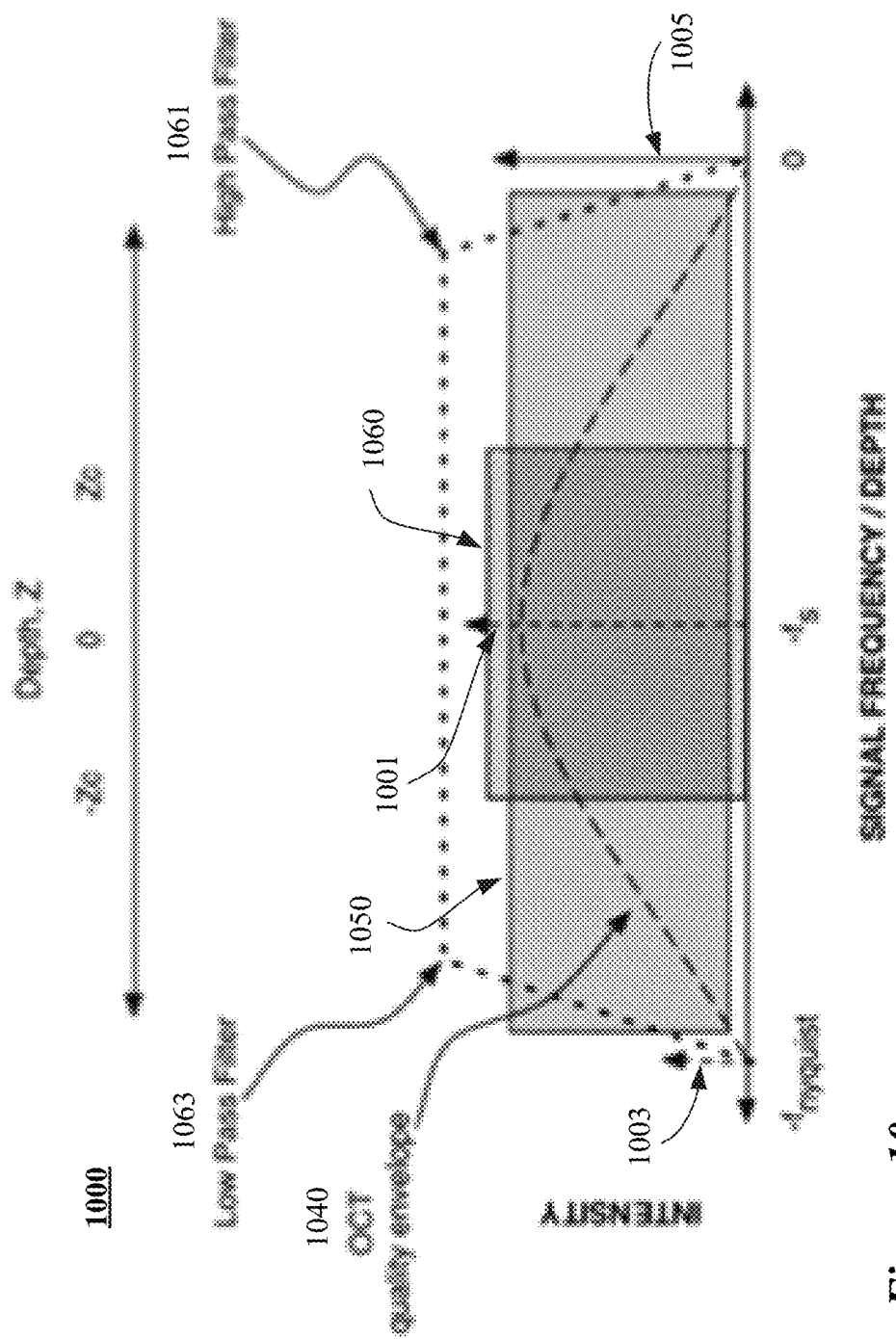
FIG. 10 illustrates another plot of a sampling range and corresponding displayed imaging range in accordance with the present disclosure.

FIG. 10 is a plot 1000 graphically illustrating a shifting of the frequency band by a carrier frequency (fs) 1001 in accordance with the present disclosure. In general, the frequency shift depicted is negative. More specifically, the frequency shift is reversed with respect to the frequency shift depicted in FIG. 6. Such a shift may be implemented by, for example, reversing the direction of the wavelength sweep, or using a negative frequency shift in the acousto-optical frequency shifter, or an alternative receiver design where the sample/reference arm phase shift is reversed during their interaction at a coupler or beam splitter. As a result, more negative frequencies correspond to deeper depths of imaging while more positive frequencies correspond to shallower imaging depths.

As depicted, the carrier frequency (fs) 1001 has been selected to extend the Nyquist frequency ($-f_{nyquist}$) 1003 beyond a lower bound of an OCT quality envelope 1040. In particular, the sampling range 1050 includes a set of frequencies bound by the Nyquist frequency ($-f_{nyquist}$) 1003 and the zero-frequency DC limit 1005. With some examples, reflections due to imaging optics (e.g., as illustrated in FIG. 9) occur on the low-pass filter 1063 side of the sampling range 1050. As a result, the low-pass filter 1063 provides an image having significantly greater attenuation and no ambiguity or foldover resulting from shallow reflections (e.g., as illustrated in FIG. 9). However, in some cases the negative frequency-shift, or the negative carrier frequency (fs) 1001 may increase the intensity of foldover artifacts resulting from the sample itself. More particularly, as the sample depths are on the high-pass filter 1061 or the zero-frequency DC limit 1005 side of the frequency band, such artifacts may be increased.

Figure 11:
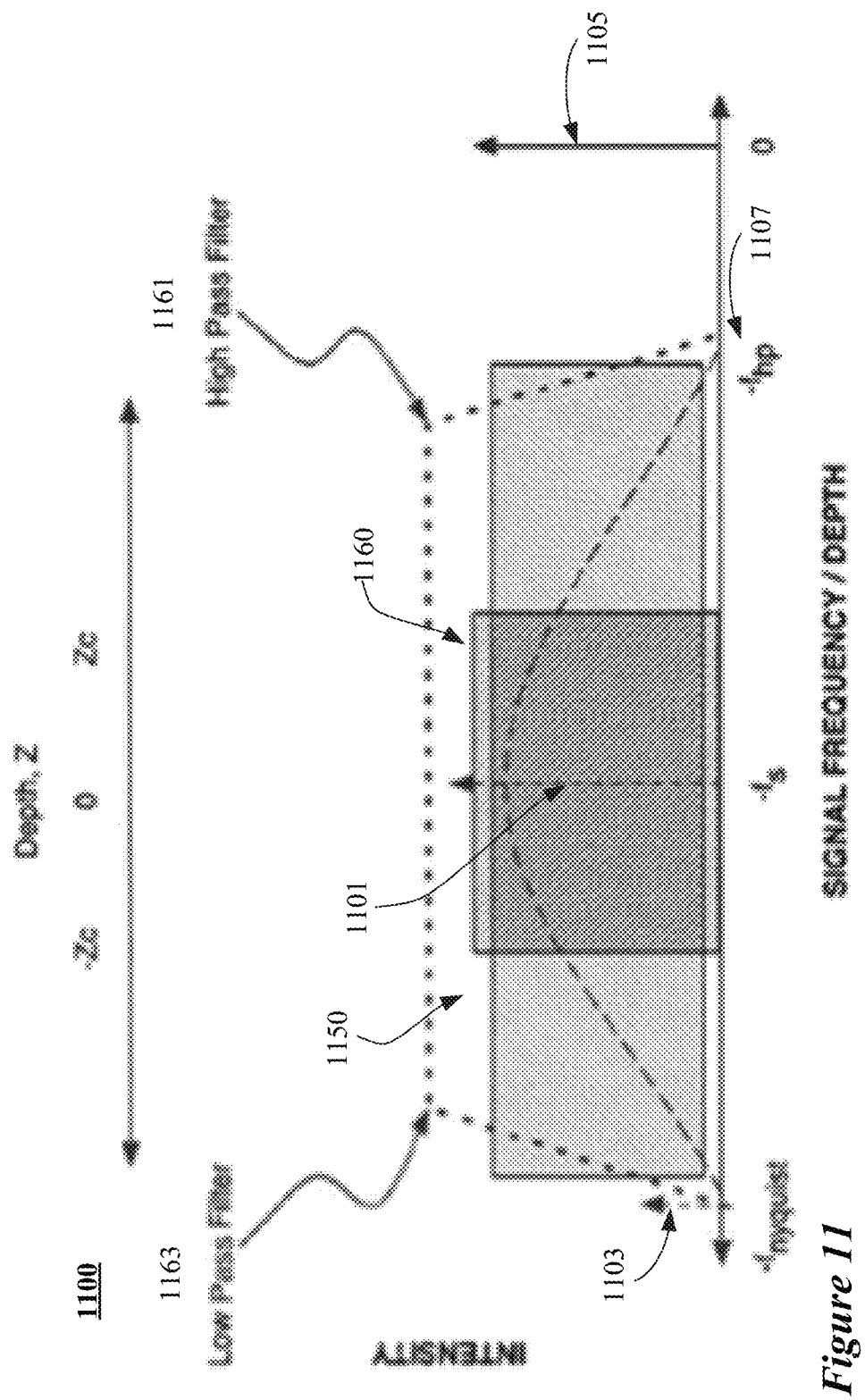
FIG. 11 illustrates another plot of a sampling range and corresponding displayed imaging range in accordance with the present disclosure.

FIG. 11 is a plot 1100 graphically illustrating an embodiment where the carrier frequency is selected such that the sample range is shifted away from the zero-frequency DC limit 1105. The embodiment shown in FIG. 11 may be implemented to reduce or eliminate sample-originated foldover artifacts arising from negative frequency shifts.

As depicted, the carrier frequency (fs) 1101 has been selected to extend the Nyquist frequency ($-f_{nyquist}$) 1103 beyond a lower bound of an OCT quality envelope 1140 but moves the sampling range 1150 away from the zero-frequency DC limit 1105. In particular, the carrier frequency (fs) 1101 is no longer approximately ½ nyquist, but instead may be selected such that the sampling range 1150 extends from the first frequency ($-f_{hp}$) 1107 to the Nyquist frequency ($-f_{nyquist}$) 1103. The high-pass filter 1161 may be implemented to filter frequencies between the zero-frequency DC limit 1105 and the first frequency ($-f_{hp}$) 1107. As such, an increased resilience to foldover artifacts due to the positive/negative frequency ambiguity of 2×fhp may be realized. In some examples, the carrier frequency (fs) 1101 may be selected to be somewhere between the zero-frequency DC limit 1105 and the nyquist frequency.

It is important to note, that although utilization of the carrier frequency to provide additional shifting of the sampling range disclosed in the context of negative frequency shifts, this is not intended to be limiting. For example, a carrier frequency may be implemented to provide additional frequency shift as described herein on conjunction with the systems described with respect to FIG. 8 for example.

FIGS. 12A-12D illustrate example images acquired using an OCT system, and in particular, depict advantages enabled by various embodiments of the present disclosure.

Figure 3:
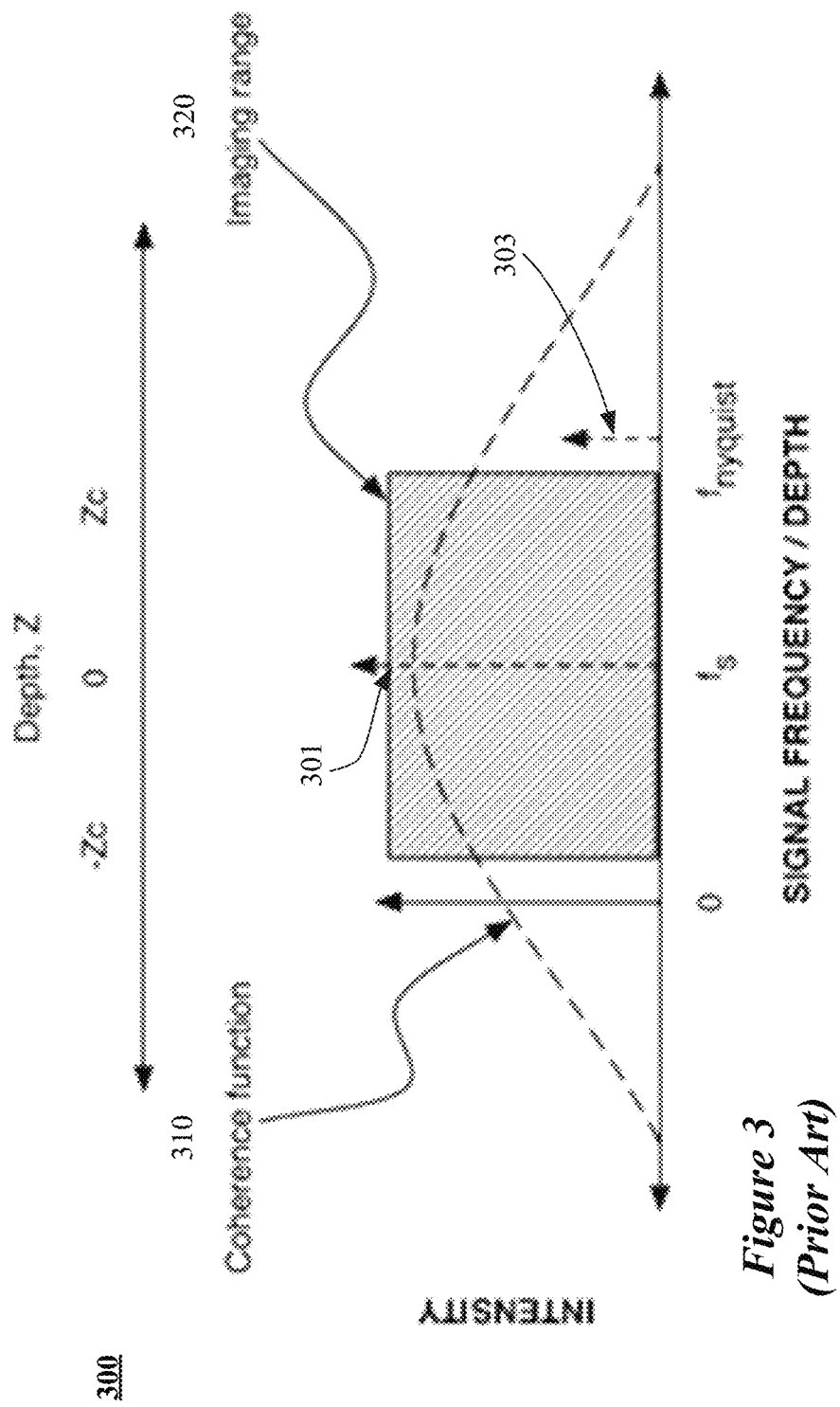
FIG. 3 illustrates a plot of a coherence function and associated imaging range due to a shifting of the frequency band by a carrier frequency.
Figure 12A:
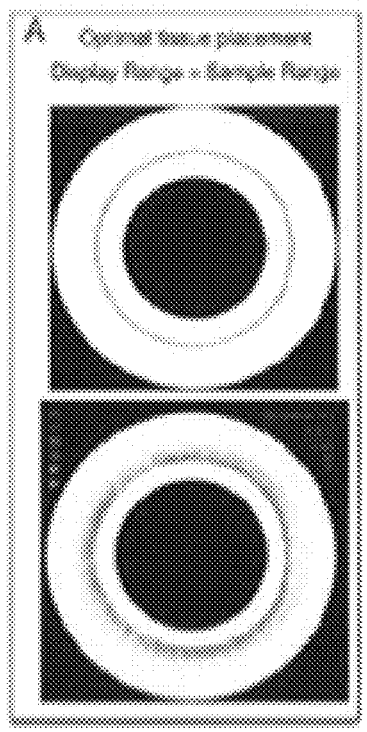
FIGS. 12A-12B illustrate example images acquired using an OCT system similar to the system described with respect to FIGS. 1-4.

Turning more specifically to FIG. 12A, an idealized image 1210 is illustrated. The idealized image may result from optimal sample placement and imaging utilizing the conventional configuration of FIG. 3 and that described in the '497 patent referenced above. As will be appreciated, the idealized image 1210 of FIG. 12A lacks foldover artifacts; however, such optimal sample placement is difficult or even impossible to achieve in practice.

Figure 4:
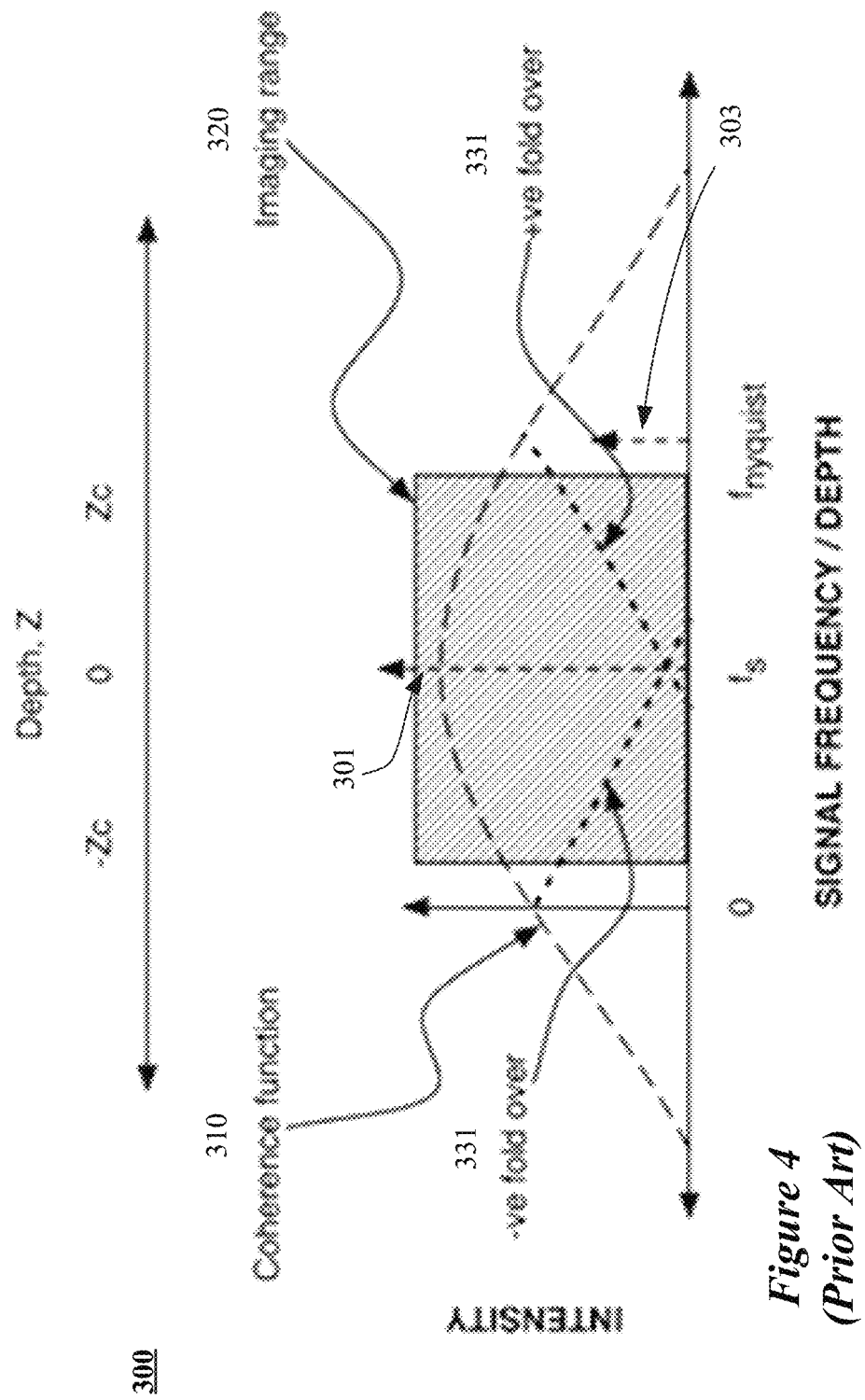
FIG. 4 illustrates a plot of the imaging range of FIG. 3 showing aliasing artifacts.
Figure 12B:
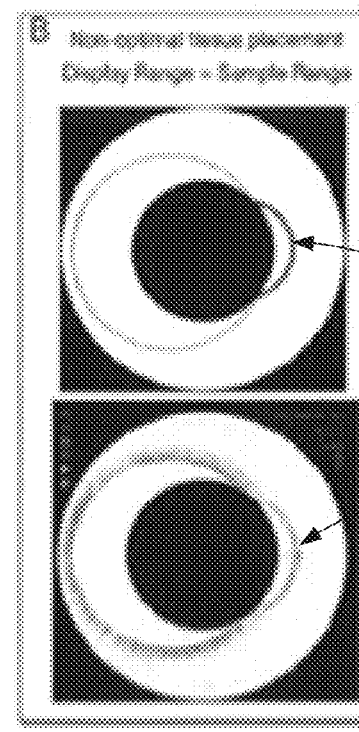

Turning more specifically to FIG. 12B, a non-optimally placed image 1220 is illustrated. The non-optimally placed image 1220 was obtained utilizing the same configuration as the idealized image 1210. However, as depicted, the non-optimally placed image 1220 includes foldover artifacts 1221 resulting from non-optimal sample placement. Such foldover artifacts are also depicted in FIG. 4 (e.g., refer to the artifacts 331). As will be appreciated, non-optimal sample placement may result from, for example, the sample arm not being positioned at a substantially constant distance from the surface of the sample or tissue being imaged over a series of scans. As shown, the foldover artifacts lead to spurious imaging data on at least a portion of the OCT scan.

Figure 12C:
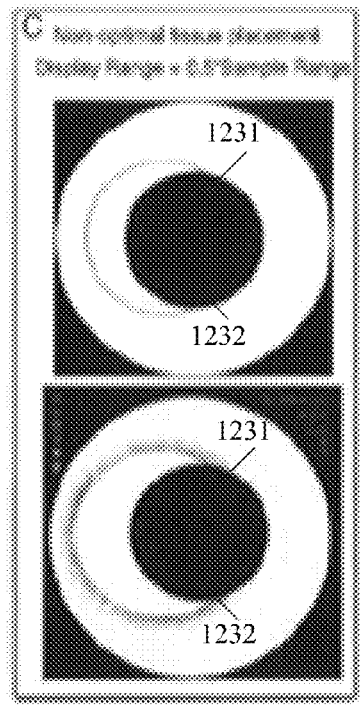
FIGS. 12C-12D illustrate example images acquired using an OCT system in accordance with the present disclosure.

Turning more specifically to FIG. 12C, a non-optimally placed image 1230 is illustrated. The image 1230 was obtained utilizing various embodiments of the present disclosure. In particular, the image 1230 was obtained wherein the displayed imaging range was generated to be approximately 50% of the sampling range. As can be seen, foldover artifacts have been eliminated. In particular, selection of the carrier frequency such that the sampling range is bound by the Nyquist frequency and the zero-frequency DC limit and then generating the displayed imaging range as a subset of the frequencies from the sampling range has substantially reduced and/or eliminated aliasing and foldover artifacts.

Figure 12D:
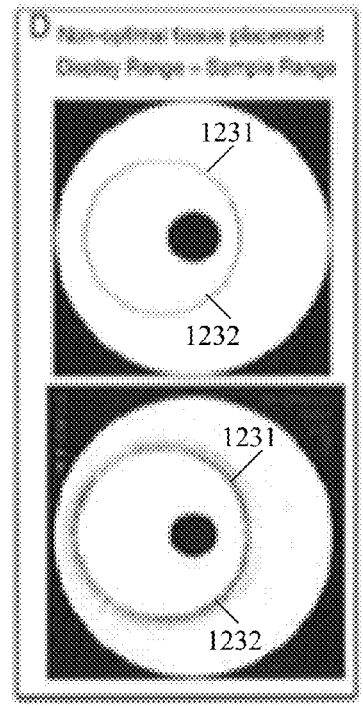

As will be appreciated, however, the reduced displayed imaging range (e.g., as compared to the sampling range) may result in a portion of the scan of a non-optimally placed sample not being displayed. In particular, as can be seen from FIG. 12C, portions of the scan between points 1231 and 1232 are cut off. FIG. 12D illustrates the same scan of a non-optimally placed sample with the display range being set to the full imaging range. As shown, the depth range of the displayed scan is increased compared to the scan of FIG. 12C, revealing the portion (e.g., between points 1231 and 1232) of the scan previously lost due to non-optimal sample placement.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:
1. A method of optically imaging a sample utilizing a frequency-domain optical coherence tomography (OCT) system comprising a wavelength-swept light source, the method comprising the steps of:
  illuminating the sample with a first portion of light emitted by the wavelength-swept light source;
  illuminating a reference plane with a second portion of light emitted by the wavelength-swept light source;
  shifting a frequency of at least one of the first portion of light or the second portion of light to define a sampling range including a set of frequencies; and generating a displayed imaging range from the sampling range, the displayed imaging range consisting essentially of only a subset of the set of frequencies within the sampling range.

2. The method of claim 1, wherein the sampling range (i) extends from a first frequency to a second frequency and (ii) is substantially centered on a carrier frequency.

3. The method of claim 2, wherein the second frequency has a numerical value greater than a numerical value of the first frequency.

4. The method of claim 2, wherein the displayed imaging range (i) extends from a third frequency, having a numerical value greater than a numerical value of the first frequency, to a fourth frequency, having a numerical value less than a numerical value of the second frequency, and (ii) is substantially centered on the carrier frequency.

5. The method of claim 4, wherein the fourth frequency has a numerical value that is greater than a numerical value of the third frequency.

6. The method of claim 2, wherein the carrier frequency is negative.

7. The method of claim 6, wherein the step of shifting a frequency of at least one of the first portion of light or the second portion of light comprises (i) using a negative frequency shift in an acousto-optical frequency shifter or (ii) reversing a phase shift associated with a sample arm and a reference arm.

8. The method of claim 1, wherein the step of shifting the frequency of at least one of the first portion of light or the second portion of light comprises:
determining a carrier frequency; and
shifting the frequency of the first portion of light based on the determined carrier frequency,
wherein a Nyquist frequency corresponding to the first portion of light is extended beyond either an upper or a lower bound of an OCT quality envelope corresponding to the first portion of light.

9. The method of claim 8, wherein a lower bound of the OCT quality envelope is greater than a zero-frequency DC limit of the first portion of light.

10. The method of claim 9, wherein the step of generating the displayed imaging range from the sampling range comprises omitting frequencies from the set of frequencies where aliasing occurs.

11. The method of claim 9, wherein the subset of frequencies in the displayed imaging range includes between 5 and 95 percent of the frequencies in the set of frequencies in the sampling range.

12. The method of claim 9, wherein the subset of frequencies in the displayed imaging range includes between 25 and 75 percent of the frequencies in the set of frequencies in the sampling range.

13. The method of claim 9, wherein the subset of frequencies in the displayed imaging range includes between 40 and 60 percent of the frequencies in the set of frequencies in the sampling range.

14. The method of claim 8, further comprising shifting the frequency of the second portion of light based on the determined carrier frequency.

15. A method of optically imaging a sample utilizing a frequency-domain optical coherence tomography (OCT) system comprising (i) an optical source for emitting output light over a range of wavelengths and (ii) an interferometer for detecting interference over a sampling range of frequencies each associated with a different depth within the sample, the method comprising:
illuminating the sample with a first portion of the output light;
illuminating a reference plane with a second portion of the output light; and
associating larger depths within the sample with more negative frequencies within the sampling range;
wherein the sampling range extends from a first frequency to a second frequency and is substantially centered on a carrier frequency.

16. The method of claim 15, further comprising generating an image of the sample based on a displayed imaging range, the displayed imaging range consisting essentially of a subset of the frequencies of the sampling range.

17. The method of claim 15, wherein the step of associating larger depths within the sample with more negative frequencies within the sampling range comprises shifting a frequency of at least one of the first portion of light or the second portion of light by a negative carrier frequency.

18. The method of claim 17, wherein the second portion of light is shifted by the carrier frequency such that a corresponding sampling range extends from a first frequency to a Nyquist frequency, wherein the first frequency is different than the zero-frequency DC limit.

19. The method of 15, the method further comprising filtering reflections of the first portion of light from the sample with at least one of a high-pass filter and a low-pass filter.

* * * * *